(12) United States Patent
Ha et al.

(10) Patent No.: US 8,586,752 B1
(45) Date of Patent: Nov. 19, 2013

(54) CRYSTALLINE S-OMEPRAZOLE STRONTIUM HYDRATE, METHOD FOR PREPARING SAME, AND PHARMACEUTICAL COMPOSITION CONTAINING SAME

(71) Applicant: Hanmi Science Co., Ltd, Hwaseong-si (KR)

(72) Inventors: Tae Hee Ha, Suwon-si (KR); Hee Sook Oh, Seoul (KR); Won Jeoung Kim, Suwon-si (KR); Chang Hee Park, Yongin-si (KR); Eun Young Kim, Suwon-si (KR); Young Hoon Kim, Seoul (KR); Kwee Hyun Suh, Suwon-si (KR); Gwan Sun Lee, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 0 days.

(21) Appl. No.: 13/943,168

(22) Filed: Jul. 16, 2013

Related U.S. Application Data

(60) Division of application No. 12/914,032, filed on Oct. 28, 2010, now Pat. No. 8,513,426, which is a division of application No. 12/425,499, filed on Apr. 17, 2009, now Pat. No. 8,106,076, which is a continuation of application No. 11/374,034, filed on Mar. 14, 2006, now Pat. No. 7,576,219.

(30) Foreign Application Priority Data

Oct. 26, 2005 (KR) ........................ 10-2005-0101059

(51) Int. Cl.
*C07D 401/12* (2006.01)
(52) U.S. Cl.
USPC ....................................... 546/273.7
(58) Field of Classification Search
USPC ....................................... 546/273.7
See application file for complete search history.

(56) References Cited

U.S. PATENT DOCUMENTS

| | | |
|---|---|---|
| 5,714,504 A | 2/1998 | Lindberg et al. |
| 5,877,192 A | 3/1999 | Lindberg et al. |
| 6,369,085 B1 | 4/2002 | Cotton et al. |
| 6,627,646 B2 | 9/2003 | Bakale et al. |

FOREIGN PATENT DOCUMENTS

| | | |
|---|---|---|
| JP | 59-167587 A | 9/1984 |
| JP | 07-509499 A1 | 10/1995 |
| JP | 2002-501529 A | 1/2002 |
| WO | 2004/099182 A1 | 11/2004 |
| WO | 2005/011692 A1 | 2/2005 |
| WO | 2006/120520 A1 | 11/2006 |
| WO | 2007/049914 | 5/2007 |

OTHER PUBLICATIONS

Chemical & Engineering News, Feb. 2003, pp. 32-35.
Brittain, Harry G., "Structural Aspects of Hydrates and Solvates," Polymorphism in Pharmaceutical Solids, Ch. 4, 1999, pp. 1-2, 125-181, 183-226.
U.S. Pharmacopies #23, National Formulary #18 (1995), pp. 1843-1844.
Concise Encyclopedia Chemistry, 1993, pp. 872-873.
Vippagunta, Sudha R., "Crystalline solids," Advanced Drug Delvery Reviews, 48, 2001, pp. 3-26.
Doelker, E., "Physicochemical Behaviors of Active Substances Their Consequences for the Feasiblity and the Stability of Pharmaceutiacl Forms," S.T.P. Pharma Pratiques, 9:5, 1999, 399-409 (with English translation of pp. 1-39).
CMU Seed Fund Project on Detection and Control of Pharmaceutical Polymorphism, Carnegie Mellon—The Dept. of Physics, 2002.
Singhal, Dharmendra, et al., "Drug polymorphism and dosage form design: a practical perspective," Advanced Drug Delivery Reviews, 56, 2004, pp. 335-347.
Caira, M.R., "Crystalline Polymorphism of Organic Compounds," Topics in Current Chemistry, 198, 1998, pp. 184-208.
Muzaffar, N.A., et al., "Polymorphism and Drug Availability," J. of Pharm. (Lahore), 1:1, 1979, pp. 59-66.
Jain, N.K. et al., "Polymorphism in Pharmacy," Indian Drugs, 23:6, 1986, pp. 315-329.
Taday, P.F., et al., "Using Terahertz Pulse Spectroscopy to Study the Crystalline Structure of a Drug: A Case Study of the Polymorphs of Ranitidine Hydrochloride," J. of Pharm. Sci., 92:4, Apr. 2003, pp. 831-838.
Otsuka, M., et al., "Effect of Polymorphic Forms of Bulk Powders on Pharmaceutical Properties of Carbamazepine Granules," Chem. Pharm. Bull., 47:6, 1999, pp. 852-856.
Japanese Patent Office, Japanese Office Action issued in corresponding JP Application No. 2008-537592, dated Dec. 27, 2011.
Wermuth et al., "The Practice of Medicinal Chemistry," Academic Press, 1999, vol. 9, No. 25, pp. 347-365, p. 452, and p. 453.

*Primary Examiner* — Patricia L Morris
(74) *Attorney, Agent, or Firm* — Sughrue Mion, PLLC

(57) ABSTRACT

Disclosed are a crystalline S-omeprazole strontium hydrate for the prevention or treatment of gastric acid-related diseases, which has high optical purity, theremostability, solubility and nonhygroscopicity, a method for preparing same, and a pharmaceutical composition containing same.

7 Claims, 2 Drawing Sheets

CRYSTALLINE S-OMEPRAZOLE STRONTIUM HYDRATE, METHOD FOR PREPARING SAME, AND PHARMACEUTICAL COMPOSITION CONTAINING SAME

This is a divisional application of U.S. Ser. No. 12/914,032 filed on Oct. 28, 2010 (now U.S. Pat. No. 8,513,426), which is a divisional application of U.S. Ser. No. 12/425,499 filed on Apr. 17, 2009 (now U.S. Pat. No. 8,106,076), which is a continuation application of U.S. Ser. No. 11/374,034 filed on Mar. 14, 2006 (now U.S. Pat. No. 7,576,219), which claim priority from Korean patent application 10-2005-0101059 filed on Oct. 26, 2005, all of which are incorporated herein by reference.

FIELD OF THE INVENTION

The present invention relates to a crystalline S-omeprazole strontium hydrate having improved optical purity, thermal stability, solubility and non-hygroscopicity, a method for preparing same, and a pharmaceutical composition containing same.

DESCRIPTION OF THE PRIOR ART

Omeprazole, 5-methoxy-2-[[(4-methoxy-3,5-dimethyl-2-pyridinyl)methyl]sulfinyl]-1H-benzimidazole having the structure of formula (II) is known as a $H^+/K^+$-ATPase or proton pump inhibitor which is effective in inhibiting gastric acid secretion to protect gastrointestinals cells (see EP Patent No. 0 005 129), and its commercial formulations, Losec® and Prilosec® (AstraZeneca AB), are marketed as medicaments for prevention and treatment of gastric acid-related disorders. This omeprazole should be formulated as enteric coated form because it has a structurally neutral molecule and thus it is thermally and chemically unstable under a condition below neutral pH value.

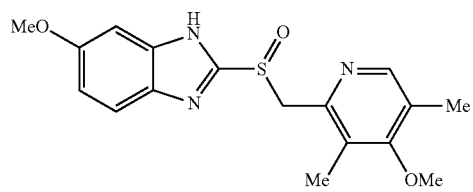

(II)

U.S. Pat. No. 4,738,974 discloses omeprazole salts and hydrates thereof, e.g., lithium, sodium, potassium, magnesium, calcium, titanium, ammonium, and guanidine salts. Such omeprazole salts are much more stable than omeprazole in the neutral form.

Omeprazole is a racemic mixture composed of equal amounts of R- and S-enantiomers. S-omeprazole of formula (III) is much more preferred over the R-isomer in the treatment of gastric or duodenal ulcer, gastroesophageal reflux disease, etc., because the R-isomer tends to be metabolized as inactive metabolites in the irregular variations. Accordingly, there have been many attempts to develop a method for preparing pure S-omeprazole which is substantially free of R-omeprazole.

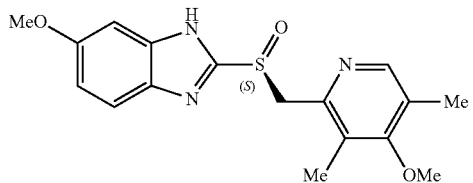

(III)

For example, racemic omeprazole has been resolved to isolate the S-isomer by a high performance liquid chromatography (see Erlandsson et al., Journal of Chromatography, 1990, 535, 305-319), and a process for preparing each of the omeprazole enantiomers is disclosed in PCT Publication No. WO 1992/08716. However, the separated S-omeprazole products have not been regarded as a stable solid of the pharmaceutically required purity. U.S. Pat. No. 6,162,816 discloses a crystalline S-omeprazole, but even this crystalline form of S-omeprazole is not sufficiently stable.

U.S. Pat. Nos. 5,714,504 and 5,693,818 disclose S-omeprazole salts and hydrates thereof, e.g., lithium, sodium, potassium, magnesium, calcium, and ammonium salts. U.S. Pat. Nos. 6,369,085 and 6,511,996 disclose the crystalline potassium salt as well as magnesium salt dihydrate and trihydrate of S-omeprazole, together with their polymorphs. These S-omeprazole salts have stability superior to S-omeprazole itself.

Now, S-omeprazole salts with sodium, potassium and magnesium, or hydrates thereof are commercially marketed with the trade name Nexium®(AstraZeneca AB) as a medicament for prevention and treatment of ulcer. The sodium and potassium salts are preferred for injectable administration because of their good solubility, but they are unsuitable for oral administration due to their hygroscopicity. On the other hand, non-hygroscopic S-omeprazole magnesium trihydate is preferred in terms of oral administration of a solid form of omeprazole, but it is not easy to achieve the optical purity required pharmaceutically. Accordingly, S-omeprazole magnesium trihydate has been subjected to the salt exchange with the optically pure sodium or potassium salt prepared in advance to achieve satisfactory therapeutic effects (see Cotton et al., Tetrahedron Asymmetry, 2000, 11, 3819-3825).

PCT Publication Nos. WO 2004/099182, WO 2005/011692, WO 2003/074514, WO 2005/023796 and WO 2005/023797 disclose S-omeprazole salts of barium, zinc, t-butylamine, adamantaneamine and α-methylcyclohexanemethane amine, but, these salts are no better than S-omeprazole magnesium trihydrate in terms of solubility, crystallinity, hygroscopicity, stability and optical purity.

In view of the previous art, therefore, there has been a need to develop an improved salt of S-omeprazole for oral administration.

Strontium is an alkaline earth metal of IIA group and it exists in nature in the form of 4 isotopes, $^{88}Sr$ (82.58%), $^{87}Sr$ (7.00%), $^{86}Sr$ (9.86%) and $^{84}Sr$ (0.56%). It is also known that strontium exerts no safety problems even at a dose of 633 mg/kg/day in rats (see P. J. Marie et al., Mineral & Electrolyte Metabolism, 1985, 11, 5-13). Strontium is reported to be ingested by people in an average amount of about 3.3 mg/day per 70 kg body weight during the course of everyday life (see Report of Toxicological Profile for Strontium, U.S. Department of Health and Human Services, 2004). It is further known that strontium supports calcium metabolism in bone tissues to promote the bone formation and inhibit the resorption of bone tissues (see S. P. Nielsen, *Bone*, 2004, 35, 583-588). As a typical example of strontium salts which have been pharmaceutically used, strontium ranelate, the salt of strontium with ranelic acid is known. However, there is so far no salt of strontium with weak acidic benzimidazole derivatives including omeprazole.

The present inventors have endeavored to develop a novel salt of S-omeprazole and found that a crystalline S-omeprazole strontium hydrate has much improved optical purity, thermo-stability, non-hygroscopicity and solubility over conventional salts.

SUMMARY OF THE INVENTION

It is a primary object of the present invention to provide a crystalline S-omeprazole strontium hydrate and a method for preparing same.

In accordance with one aspect of the present invention, there is provided a crystalline S-omeprazole strontium hydrate, more specifically, the crystalline S-omeprazole strontium hydrate of formula (I):

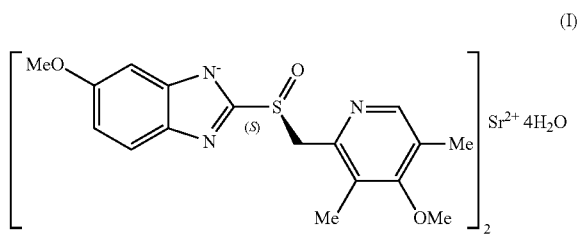

(I)

In accordance with another aspect of the present invention, there is provided a method for preparing the crystalline S-omeprazole strontium hydrate of formula (I), which comprises the step of adding strontium hydroxide or another strontium salt to a neutral or basic solution containing S-omeprazole of formula (III) and stirring the resulting mixture:

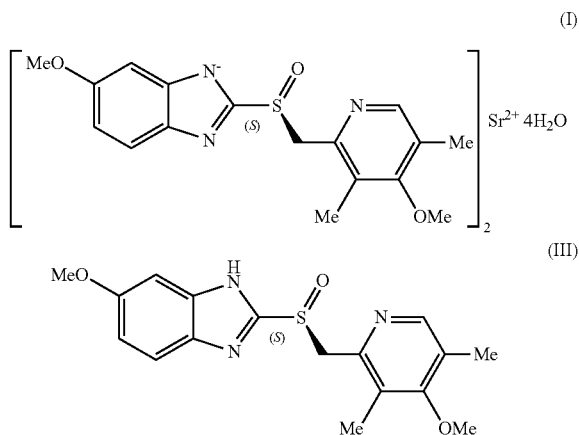

(I)

(III)

In accordance with still another aspect of the present invention, there is provided a pharmaceutical composition comprising the crystalline S-omeprazole strontium hydrate as an active ingredient for the prevention or treatment of gastric acid-related disorders.

BRIEF DESCRIPTION OF THE DRAWINGS

The above and other objects and features of the present invention will become apparent from the following description of the invention taken in conjunction with the accompanying drawings, which respectively show.

DETAILED DESCRIPTION OF THE INVENTION

The S-omeprazole strontium of formula (I) of the present invention is a novel salt of S-omeprazole, which is optically purer, thermally more stable, less hygroscopic and more soluble than any of magnesium salts.

Figure 1:
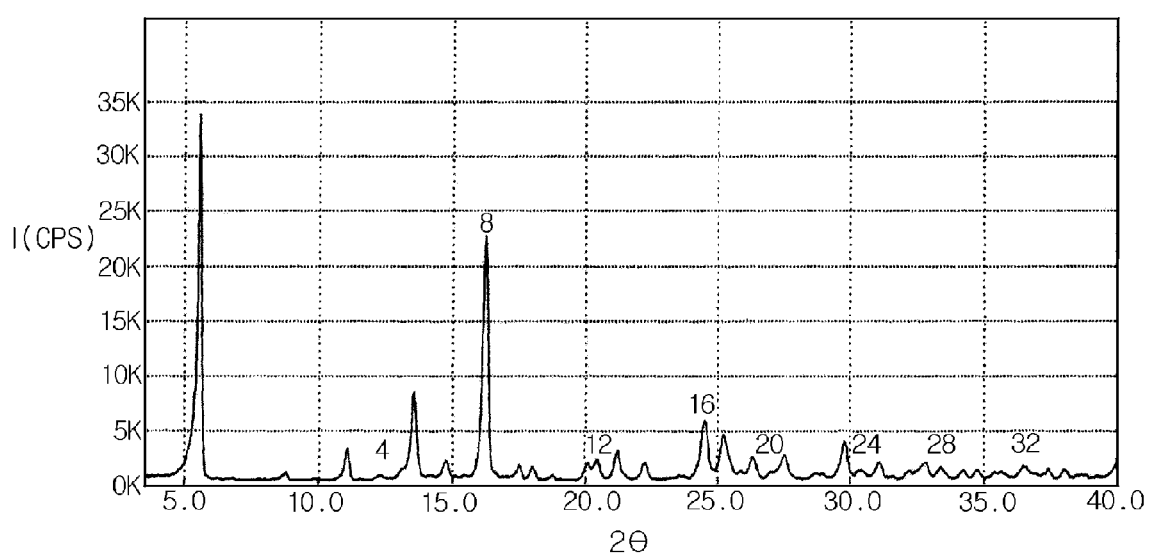
FIG. 1: a X-ray powder diffraction (XPRD) spectrum of the inventive crystalline S-omeprazole strontium tetrahydrate.
Figure 2:
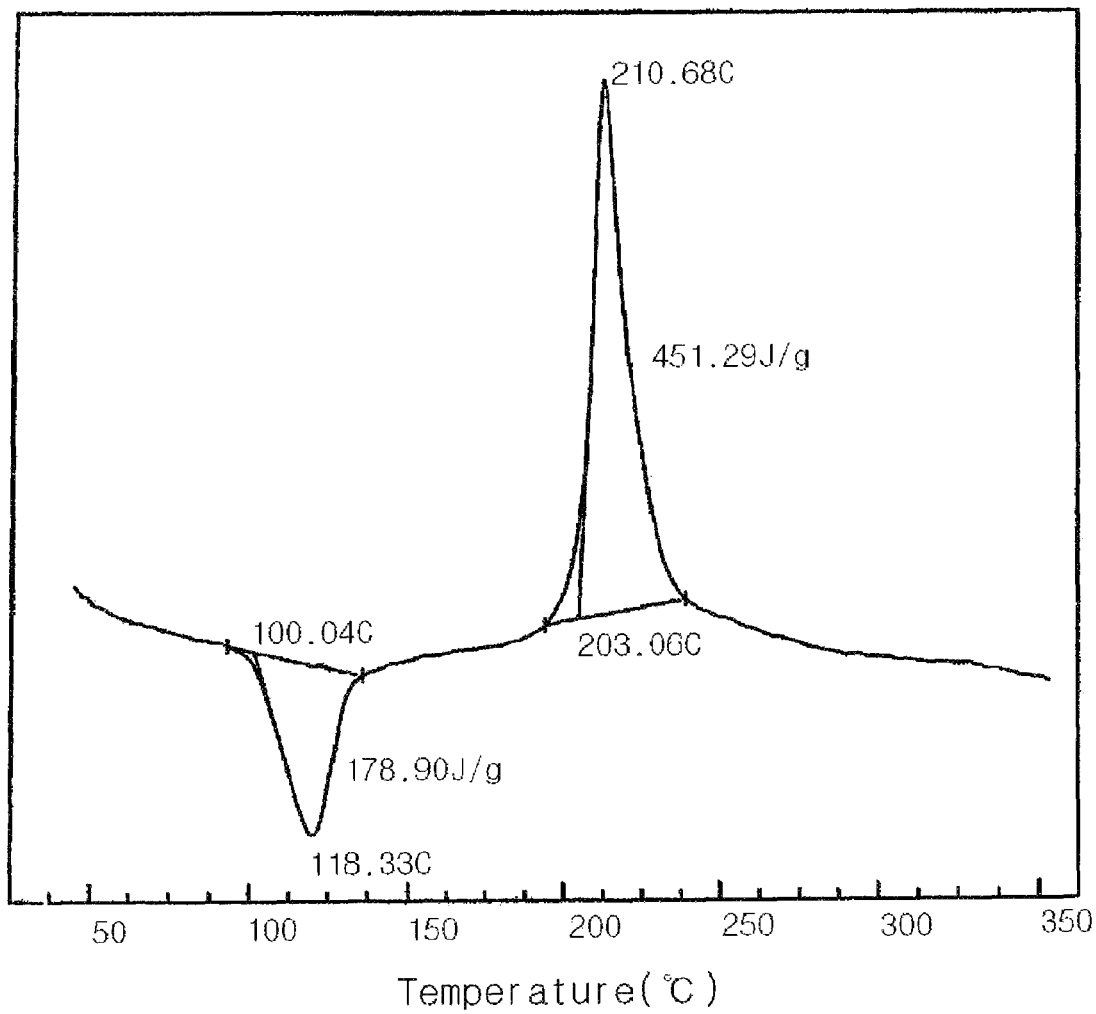
FIG. 2: a differential scanning calorimeter (DSC) curve of the inventive crystalline S-omeprazole strontium tetrahydrate.

The inventive S-omeprazole strontium salt forms a crystalline tetrahydrate structure in which two S-omeprazole molecules and four $H_2O$ molecules are coordinated to strontium ion (II), and its powder X-ray diffraction (XRD) spectrum shows major peaks having $I/I_o$ values of at least 3% (I is the intensity of each peak; $I_o$ is the intensity of the highest peak) at 2θ±0.2 of 5.6, 11.1, 13.5, 14.8, 16.2, 17.5, 18.0, 20.1, 20.4, 21.2, 22.2, 24.5, 25.2, 26.3, 27.5, 29.8, 31.1, 32.8 and 36.5 (FIG. 1). Also, a differential scanning calorimeter curve of the S-omeprazole strontium salt obtained at 5° C./min shows an endothermic peak of about 179 J/g which starts at about 100° C. reaching its maximum point at about 118° C., as well as an exothermic peak of about 451 J/g which starts at about 203° C. reaching its peak at about 211° C. (FIG. 2). The moisture content of the S-omeprazole strontium salt determined by using Karl-Fischer titrator is 8.0 to 9.5% (calculated for tetrahydrate, 8.49%) and the observed melting point thereof is about 202° C.

Such crystalline S-omeprazole strontium hydrate satisfies the pharmaceutically required stability since it can maintain the initial moisture content, purity and crystallinity under a long-term storage condition (25° C. under 60% relative humidity, exposed), an accelerated aging condition (40° C. under 75% relative humidity, exposed) and an stressed condition (60° C. and 75% relative humidity, closed) for 2 to 4 weeks.

Further, the inventive crystalline S-omeprazole strontium hydrate may be pharmaceutically preferred in terms of water solubility over the other salt of S-omeprazole. For example, it has a water solubility of about 17.6 mg/ml, which is at least 10 times higher than that of S-omeprazole magnesium trihydrate.

In accordance with the present invention, the crystalline S-omeprazole strontium hydrate of formula (I) may be prepared by adding strontium hydroxide or another strontium salt to a neutral or basic solution comprising S-omeprazole of formula (III).

Specifically, the crystalline S-omeprazole strontium hydrate may be prepared by adding strontium hydroxide to a neutral solution containing S-omeprazole of formula (III), stirring the resulting mixture until precipitates form, and filtering and drying the resulting precipitates by a conventional method. The neutral solution means a solution prepared by dissolving or suspending S-omeprazole in an organic solvent selected from methanol, ethanol, 1-propanol, 2-propanol, acetonitrile, tetrahydrofuran and acetone, preferably, methanol and acetone, or in a mixture of one of the organic solvents and water, preferably, having a mix ratio having a mix ratio of 99:1 to 50:50 (v/v). In the present invention, strontium hydroxide is preferably used in an amount of 0.5 to 0.75 molar equivalents based on 1 molar equivalent of the S-omeprazole of formula (III). Also, the stirring procedure may be carried out at a temperature ranging from 0° C. to the boiling point of the solvent used for 30 minutes to 24 hours.

Alternatively, the crystalline S-omeprazole strontium hydrate may be prepared by adding a reactive strontium salt to a basic solution containing S-omeprazole of formula (III) and a base, stirring the resulting mixture until precipitates form, and filtering and drying the resulting precipitates by a conventional method. The reactive strontium salt may be selected from strontium chloride, strontium bromide, strontium sulfate, strontium nitrate, strontium perchlorate, strontium acetate, strontium carbonate and strontium oxalate, preferably strontium chloride and strontium acetate. The basic solution means a solution prepared by dissolving or suspending S-omeprazole and a base in an organic solvent selected from methanol, ethanol, 1-propanol, 2-propanol, acetonitrile, tetrahydrofuran and acetone, preferably, methanol and acetone or in a mixture of one of the organic solvents and water, preferably, having a mix ratio of 99:1 to 50:50 (v/v). The base may be selected from lithium hydroxide, sodium hydroxide, potassium hydroxide, ammonia, methylamine, ethylamine, propylamine, dimethylamine, diethylamine, trimethylamine and triethylamine, preferably sodium hydroxide and potassium hydroxide. In this embodiment, the base is preferably used in an amount ranging from 1 to 3 molar equivalents based on 1 mole of S-omeprazole of formula (III) and the amount of the reactive strontium salt is preferably in the range of 0.5 to 0.75 molar equivalents based on 1 molar equivalent of the base. The stirring may be conducted at a temperature ranging from 0° C. to the boiling point of the solvent used for 30 minutes to 24 hours.

The neutral or basic solution used in the present invention may be obtained during the preparation of S-omeprazole according to any of the known methods such as the method disclosed in Korean Patent Application No. 2005-68761. It is preferred that the neutral or basic solution is used an amount ranging from 1 to 20 ml, preferably 3 to 10 ml based on 1 g of S-omeprazole of formula (III).

In accordance with the above method of the present invention, S-omeprazole salts having high optical purity can be obtained even when an optically impure S-omeprazole is used as a starting material.

Thus, the inventive crystalline S-omeprazole strontium hydrate of formula (I) having a high optical purity of at least 99.0% enantiomeric excess (ee) shows non-hygroscopicity and good stability against moisture and heat, so that it can be pharmaceutically used for the prevention or treatment of gastric acid-related disorders such as gastroesophageal reflux disease, gastroenteritis and gastric ulcer due to hyperacidity.

A pharmaceutical composition comprising the inventive crystalline S-omeprazole strontium hydrate as an active ingredient may be administered via various routes including oral, rectal and injectable application, preferably the oral route.

For oral administration, the pharmaceutical composition of the present invention may be in the form of tablets, capsules, pills, and the like, and may be formulated with pharmaceutically acceptable carriers, diluents or excipients.

Examples of suitable carriers, diluents and excipients are excipients such as starches, sugar and mannitol; filling agents or increasing agents such as calcium phosphate and silica derivatives; binding agents such as cellulose derivatives of carboxymethylcellulose or hydroxypropylcellulose, gelatin, arginic acid salt, and polyvinylpyrrolidone; lubricating agents such as talc, magnesium or calcium stearate, hydrogenated castor oil and solid polyethylene glycol; disintegrants such as povidone, croscarmellose sodium, and crospovidone; and surfactants such as polysorbate, cetyl alcohol and glycerol monostearate. Further, various pharmaceutical composition comprising a specific amount of active ingredient, together with or without additives such as said excipients, diluents or additives, may be prepared in accordance with any of the conventional procedures (see *Remington's Pharmaceutical Science*, Mack Publishing Company, Easton, Pa., 19$^{th}$ Edition, 1995).

For sterile injectable administration, the pharmaceutical composition of the present invention may be prepared by directly filling the inventive crystalline S-omeprazole strontium hydrate and a pharmaceutically acceptable carrier in vials under a sterile condition, or by filling the amorphous powder obtained by dissolving the inventive crystalline S-omeprazole strontium hydrate and a pharmaceutically acceptable carrier in sterile water and then freeze-drying in vials, which is dissolved in sterile water to be administered.

In a preferred embodiment, the pharmaceutical composition for oral administration of the present invention may contain the crystalline S-omeprazole strontium hydrate of formula (I) in an amount ranging from 0.1 to 95% by weight, preferably 1 to 70% by weight based on the total weight of the composition.

A typical daily dose of the inventive crystalline S-omeprazole strontium hydrate of formula (I) for a mammalian including human may range from about 0.5 to 500 mg/kg body weight, preferably 5 to 100 mg/kg body weight, and can be administered in a single dose or in divided doses.

The present invention will be described in further detail with reference to Examples. However, it should be understood that the present invention is not restricted by the specific Examples.

EXAMPLE

The analysis conditions of HPLC employed in Examples are listed below, and the unit "% ee" as used herein means enantiomeric excess.

Condition A: For the Measurement of the Amount of Omeprazole
  Column: Zorbax C8 XDB, 5 μm (150 mm×4.6 mm)
  Detector: 281 nm
  Flow rate: 1.0 e/minute
  Elution condition: $Na_2HPO_4$—$NaH_2PO_4$ buffer solution/$CH_3CN$=75/25 (v/v)

Condition B: For the Measurement of the Optical Purity of S-Omerprazole Strontium
  Column: Chiral-AGP, 5 μm (150 mm×4 mm)
  Detector: 280 nm
  Flow rate: 0.8 m/minute
  Elution condition: $NaH_2PO_4$ buffer solution (pH 6.5)/$CH_3CN$=10/90 (v/v)

Example 1

Preparation of S-omerprazole strontium tetrahydrate

S—Omeprazole (30.0 g, 86.9 mmol) having an optical purity of 95% ee was dissolved in 200 ml of methanol, and strontium hydroxide octahydrate (13.8 g, 51.9 mmol) dissolved in 100 ml of methanol was slowly added thereto, followed by stirring the mixture at room temperature for 3 hours. The precipitate formed was filtered, washed with 100 ml of methanol and dried at 45° C. for 12 hours, to obtain 33.8 g of the title compound (yield: 92%) as an white crystalline powder.

M.P.: 201~203° C.

Moisture content (Karl-Fisher titrator): 9.0% (calculated for tetrahydrate, 8.49%)
Strontium content (EDTA titration): 11.1% (calculated for anhydrate, 11.3%)
Omerprazole content (HPLC, condition A): 88.5% (calculated for anhydrate, 88.7%)
Optical purity (HPLC, condition B): 99.9% ee
Specific rotation, $[\alpha]D^{20}$: −31.1° (c=1.0, acetone)
$^1$H-NMR (DMSO-d$^6$): δ8.26 (s, 1H), 7.38 (d, 1H), 7.02 (bs, 1H), 6.54 (dd, 1H), 4.58 (d, 2H, J=13.3), 4.46 (d, 2H, J=13.4), 3.68 (s, 3H), 3.66 (s, 3H), 2.22 (s, 3H), 2.10 (s, 3H)
IR (KBr, cm$^{-1}$): 3422, 2991, 2831, 2364, 1638, 1611, 1569, 1561, 1476, 1444.4, 1390, 1365, 1271, 1204, 1156, 1077, 1027, 1000, 855, 844, 798, 637, 487

As depicted in the X-ray powder diffraction spectrum of the S-omeprazole strontium tetrahydrate (FIG. 1), the S-omeprazole strontium tetrahydrate is a crystal having the distinctively characteristic diffraction pattern shown in Table 1, wherein main peaks having I/I$_0$ values of at least 3% are listed.

TABLE 1

| 2θ (±2) | d | I/I$_o$ (%) |
|---|---|---|
| 5.6 | 15.9 | 100 |
| 11.1 | 8.0 | 8.6 |
| 13.5 | 6.5 | 23.5 |
| 14.8 | 6.0 | 4.5 |
| 16.2 | 5.5 | 66.5 |
| 17.5 | 5.1 | 3.4 |
| 18.0 | 4.9 | 3.2 |
| 20.1 | 4.4 | 4.4 |
| 20.4 | 4.3 | 5.3 |
| 21.2 | 4.2 | 7.8 |
| 22.2 | 4.0 | 4.3 |
| 24.5 | 3.6 | 15.4 |
| 25.2 | 3.5 | 11.6 |
| 26.3 | 3.4 | 5.4 |
| 27.5 | 3.2 | 6.3 |
| 29.8 | 3.0 | 9.8 |
| 31.1 | 2.9 | 4.2 |
| 32.8 | 2.7 | 4.3 |
| 36.5 | 2.5 | 3.2 |

2θ: angle of diffraction, d: distance within each crystal face, I/I$_0$ (%): relative intensity of peak Also, as can be seen from FIG. 2, the differential scanning calorimeter (DSC) curve obtained at 5° C./min of the S-omeprazole strontium tetrahydrate showed an endothermic peak of about 179 J/g which starts at about 100° C. reaching its maximum point at about 118° C. and an exothermic peak of 451 J/g which starts at about 203° C. reaching its maximum level at about 211° C.

Example 2

Preparation of S-Omerprazole Strontium Tetrahydrate

S-Omeprazole (10.4 g, 30.1 mmol) having an optical purity of 90% ee was dissolved in 100 ml of methanol, and strontium hydroxide octahydrate (4.6 g, 17.3 mmol) dissolved in 100 ml of methanol was slowly added thereto, followed by stirring the resulting mixture at room temperature for 3 hours. The precipitate formed was filtered, washed with 50 ml of methanol and dried at 45° C. for 12 hours, to obtain 10.7 g of the title compound (yield: 84%) as an white crystalline powder.
M.P.: 201~203° C.
Moisture content (Karl-Fisher titrator): 8.9% (calculated for tetrahydrate, 8.49%)
Strontium content (EDTA titration): 11.2% (calculated for anhydrate, 11.3%)
Omerprazole content (HPLC, condition A): 88.4% (calculated for anhydrate, 88.7%)
Optical purity (HPLC, condition B): 99.9% ee Example 3

Preparation of S-Omerprazole Strontium Tetrahydrate

S—Omeprazole (10.4 g, 30.1 mmol) having an optical purity of 80% ee was dissolved in 100 ml of methanol, and strontium hydroxide octahydrate (4.6 g, 17.3 mmol) dissolved in 50 ml of methanol was slowly added thereto, followed by stirring the resulting mixture at room temperature for 3 hours. The precipitate formed was filtered, washed with 50 ml of methanol and dried at 45° C. for 12 hours, to obtain 9.3 g of the title compound (yield: 73%) as an white crystalline powder.
M.P.: 201~203° C.
Moisture content (Karl-Fisher titrator): 8.7% (calculated for tetrahydrate, 8.49%)
Strontium content (EDTA titration): 11.2% (calculated for anhydrate, 11.3%)
Omerprazole content (HPLC, condition A): 88.5% (calculated for anhydrate, 88.7%)
Optical purity (HPLC, condition B): 99.7% ee Example 4

Preparation of S-Omerprazole Strontium Tetrahydrate

Sodium hydroxide (3.8 g, 95.0 mmol) was dissolved in 150 ml of water, and S-omeprazole (27.5 g, 79.6 mmol) having an optical purity of 90% ee was dissolved therein. Thereto, strontium chloride hexahydrate (12.7 g, 47.8 mmol) dissolved in 150 ml of methanol was slowly added, and the resulting mixture was stirred at room temperature for 3 hours. The precipitate formed was filtered, washed with a mixture of water (20 ml) and methanol (80 ml) and dried at 45° C. for 12 hours, to obtain 29.7 g of the title compound (yield: 88%) as an white crystalline powder.
M.P.: 201~203° C.
Moisture content (Karl-Fisher titrator): 8.9% (calculated for tetrahydrate, 8.49%)
Strontium content (EDTA titration): 11.35% (calculated for anhydrate, 11.3%)
Omerprazole content (HPLC, condition A): 88.6% (calculated for anhydrate, 88.7%)
Optical purity (HPLC, condition B): 99.8% ee Example 5

Preparation of S-Omerprazole Strontium Tetrahydrate

Potassium hydroxide (5.3 g, 94.5 mmol) was dissolved in 150 ml of water, and S-omeprazole (27.5 g, 79.6 mmol) having an optical purity of 95% ee was dissolved therein. Thereto, strontium chloride hexahydrate (12.7 g, 47.8 mmol) dissolved in 150 ml of methanol was slowly added, and the resulting mixture was stirred at room temperature for 3 hours. The precipitate formed was filtered, washed with a mixture of water (20 ml) and methanol (80 ml) and dried at 45° C. for 12 hours, to obtain 28.7 g of the title compound (yield: 85%) as an white crystalline powder.
M.P.: 201~203° C.
Moisture content (Karl-Fisher titrator): 9.0% (calculated for tetrahydrate, 8.49%)
Strontium content (EDTA titration): 11.3% (calculated for anhydrate, 11.3%)
Omerprazole content (HPLC, condition A): 88.5% (calculated for anhydrate, 88.7%)
Optical purity (HPLC, condition B): 99.8% ee Example 6

Preparation of S-Omerprazole Strontium Tetrahydrate

Potassium hydroxide (5.3 g, 94.5 mmol) was dissolved in 150 ml of water, and S-omeprazole (27.5 g, 79.6 mmol) having an optical purity of 95% ee was dissolved therein. 150 ml of methanol and strontium acetate (12.7 g, 47.8 mmol) dissolved in 50 ml of water were slowly added thereto, and the resulting mixture was stirred at room temperature for 3 hours. The precipitate formed was filtered, washed with a mixture of water (20 ml) and methanol (80 ml) and dried at 45° C. for 12 hours, to obtain 28.0 g of the title compound (yield: 83%) as an white crystalline powder.
M.P.: 201~203° C.
Moisture content (Karl-Fisher titrator): 8.9% (calculated for tetrahydrate, 8.49%)
Strontium content (EDTA titration): 11.2% (calculated for anhydrate, 11.3%)
Omerprazole content (HPLC, condition A): 88.5% (calculated for anhydrate, 88.7%)
Optical purity (HPLC, condition B): 99.9% ee Example 7

Preparation of S-Omerprazole Strontium Tetrahydrate

An inclusion complex of (S)-(−)-binol and S-omeprazole (optical purity: 97.0% ee) prepared according to Examples 1 to 14 of Korean Patent Application No. 2005-68761 (80 g, 126.6 mmol) was dissolved in 400 ml of methanol, and strontium hydroxide octahydrate (20 g, 75.3 mmol) was added thereto, followed by stirring the resulting mixture at room temperature for 3 hours. The precipitate formed was filtered, washed with 150 ml of methanol and dried at 45° C. for 12 hours, to obtain 49.0 g of the title compound (yield: 91%) as an white crystalline powder.
M.P.: 201~203° C.
Moisture content (Karl-Fisher titrator): 9.0% (calculated for tetrahydrate, 8.49%)
Strontium content (EDTA titration): 11.2% (calculated for anhydrate, 11.3%)
Omerprazole content (HPLC, condition A): 88.5% (calculated for anhydrate, 88.7%)
Optical purity (HPLC, condition B): 99.9% ee Example 8

Preparation of S-Omerprazole Strontium Tetrahydrate

An inclusion complex of (S)-(−)-binol and S-omeprazole (optical purity: 97.0% ee) prepared according to Examples 1 to 14 of Korean Patent Application No. 2005-68761 (50 g, 79.1 mmol) was dissolved in 500 ml of isopropyl acetate, and sodium hydroxide (3.8 g, 95.0 mmol) dissolved in 150 ml of water was thereto, followed by stirring the resulting mixture at room temperature for 3 hours. After separating isopropyl acetate, the aqueous layer was washed with 200 ml of isopropyl acetate. To the basic aqueous layer including S-omeprazole, a strontium chloride hexahydrate (12.6 g, 47.5 mmol) dissolved in 150 ml of methanol was slowly added. The solution suspended was stirred for 3 hours. The precipitate formed was filtered, washed with a mixture of water (20 ml) and methanol (80 ml) and dried at 45° C. for 12 hours, to obtain 28.5 g of the title compound (yield: 85%) as an white crystalline powder.
M.P.: 201~203° C.
Moisture content (Karl-Fisher titrator): 8.8% (calculated for tetrahydrate, 8.49%)
Strontium content (EDTA titration): 11.3% (calculated for anhydrate, 11.3%)
Omerprazole content (HPLC, condition A): 88.6% (calculated for anhydrate, 88.7%)
Optical purity (HPLC, condition B): 99.7% ee Comparative Example 1

Preparation of S-Omeprazole Magnesium Trihydrate

Magnesium trihydrate of S-omeprazole was prepared according to Example 7 of U.S. Pat. No. 6,369,085.
Specifically, potassium hydroxide (1.26 g, 22.5 mmol) was dissolved in 30 ml of water, and S-omeprazole (5.18 g, 15.0 mmol) having an optical purity of 95% ee was added thereto. Then, magnesium sulfate (1.81 g, 15.0 mmol) dissolved in 10 ml of water was slowly added to the solution, followed by stirring the resulting mixture at room temperature for 3 hours. The precipitate formed was filtered, washed with 15 ml of water, and was dried by blowing warm air at 45° C. for 12 hours, to obtain S-omeprazole magnesium trihydrate as a white crystalline powder in a yield of 95%.

Comparative Examples 2 and 3

Preparation of S-Omeprazole Magnesium Trihydrate

The procedure of Comparative Example 1 was repeated except for using S-omeprazole having an optical purity of 90% ee and 80% ee, respectively.

Experimental Example 1

Optical Purity Test

The S-omeprazole strontium tetrahydrates obtained in Examples 1 to 3 and the S-omeprazole magnesium trihydrates obtained in Comparative Examples 1 to 3, respectively, were subjected HPLC analyses under the previously described condition B, to measure the optical purities thereof. The results are shown in Table 2.

TABLE 2

| Effect of increasing optical purity | | |
|---|---|---|
| Starting material | Obtained salt of S-omeprazole | |
| (S-omeprazole) | Magnesium trihydrate | Strontium tetrahydrate |
| 80% ee | 81.4% ee (Com. Ex. 1) | 99.9% ee (Ex. 1) |
| 90% ee | 91.1% ee (Com. Ex. 2) | 99.9% ee (Ex. 2) |
| 95% ee | 95.0% ee (Com. Ex. 3) | 99.7% ee (Ex. 3) |

As shown in Table 2, the optical purities of the inventive S-omeprazole strontium tetrahydrates were markedly higher than those of the starting materials and the S-omeprazole magnesium trihydrates.

Experimental Example 2

Water-Solubility Test

The S-omeprazole strontium tetrahydrate of the present invention and the S-omeprazole magnesium trihydrate were each dissolved in deionized water to saturation. The water-solubility of each of the saturated solutions was analyzed by HPLC under the previously described condition A and the amount of each salt hydrate dissolved was measured. The results are shown in Table 3.

TABLE 3

| Salt | Solubility (mg/ml, 25° C.) | Saturation pH |
|---|---|---|
| Magnesium trihydrate | 1.5 | 9.9 |
| Strontium tetrahydrate | 17.6 | 10.2 |

As shown in Table 3, the solubility of the inventive S-omeprazole strontium tetrahydrate is at least 10 times higher than that of the known S-omeprazole magnesium trihydrate, which suggests that the inventive strontium salt is more suitable for injectable application.

Experimental Example 3

Hygroscopicity Test

The inventive S-omeprazole strontium was exposed in the naked state at 25 to 40° C. and 40 to 90% relative humidity for a period of over 15 days. The moisture contents of the inventive salt measured with a Karl-Fisher titrator at storage time 0, 3, 7 and 15 days are shown in Table 4.

TABLE 4

| | Moisture content (wt %) | | | |
|---|---|---|---|---|
| | 40% (25° C.) | 60% (25° C.) | 75% (40° C.) | 90% (35° C.) |
| 0 day | 9.0 | 9.0 | 9.0 | 9.0 |
| 3 days | 8.9 | 9.0 | 8.9 | 9.2 |
| 7 days | 8.7 | 9.2 | 9.0 | 9.3 |
| 15 days | 8.8 | 9.1 | 8.9 | 9.2 |

Calculated moisture content 8.49%

As shown in Table 4, the inventive S-omeprazole strontium tetrahydrates was less hygroscopic under a highly humid condition, and its initial moisture content was maintained under a low humidity condition.

Experimental Example 4

Heat Stability Test of the Inventive Salt

The salt of Example 1 was stored in the sealed state under a stressed condition of 60° C. and 75% relative humidity, and the remaining amounts of active S-omeprazole after 7, 14, 21 and 28 days were measured by HPLC condition A. The results are shown in Table 5.

TABLE 5

| | Amount of titrated S-omeprazole (μg/mg) |
|---|---|
| Initial | 997 |
| 7 days | 997 |
| 14 days | 998 |
| 21 days | 997 |
| 28 days | 997 |

As shown in Table 5, the inventive S-omeprazole strontium tetrahydrate is highly stable as witnessed by the result obtained under the accelerated aging condition.

While the invention has been described with respect to the specific embodiments, it should be recognized that various modifications and changes may be made by those skilled in the art to the invention which also fall within the scope of the invention as defined as the appended claims.

What is claimed is:

1. A method for preparing a crystalline S-omeprazole strontium tetrahydrate of formula (I), which comprises the step of adding a reactive strontium salt to a basic solution containing S-omeprazole of formula (III) and a base, and stirring the resulting mixture:

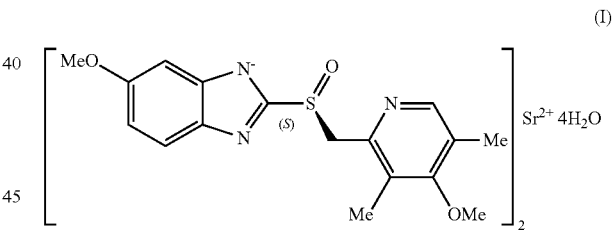

(I)

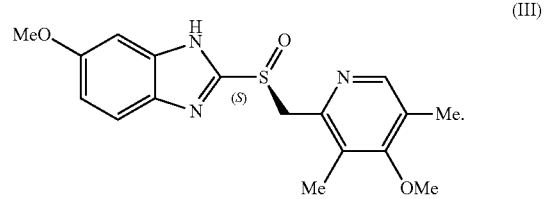

(III)

2. The method of claim 1, wherein the base is used in an amount ranging from 1 to 3 molar equivalents based on 1 molar equivalent of S-omeprazole.

3. The method of claim 1, wherein the reactive strontium salt is used in an amount ranging from 0.5 to 0.75 molar equivalents based on 1 molar equivalent of the base.

4. The method of claim 1, wherein the basic solution is prepared by dissolving or suspending S-omeprazole and a base in an organic solvent selected from the group consisting of methanol, ethanol, 1-propanol, 2-propanol, acetonitrile, tetrahydrofuran, acetone and a mixture thereof, or in a mixture of the organic solvent and water.

5. The method of claim 1, wherein the base is selected from the group consisting of lithium hydroxide, sodium hydroxide, potassium hydroxide, ammonia, methylamine, ethylamine, propylamine, dimethylamine, diethylamine, trimethylamine, triethylamine and a mixture thereof.

6. The method of claim 1, wherein the reactive strontium salt is selected from the group consisting of strontium chloride, strontium bromide, strontium sulfate, strontium nitrate, strontium perchlorate, strontium acetate, strontium carbonate, strontium oxalate and a mixture thereof.

7. The method of claim 1, wherein said S-omeprazole strontium tetrahydrate of formula (I) has X-ray powder diffraction spectrum showing major peaks having $I/I_p$ values of at least 3% at 2θ±0.2 of 5.6, 11.1, 13.5, 14.8, 16.2, 17.5, 18.0, 20.1, 20.4, 21.2, 22.2, 24.5, 25.2, 26.3, 27.5, 29.8, 31.1, 32.8 and 36.5.

\* \* \* \* \*